United States Patent [19]

Mateescu et al.

[11] Patent Number: 5,456,921
[45] Date of Patent: Oct. 10, 1995

[54] USE OF CROSS-LINKED AMYLOSE AS A MATRIX FOR THE SLOW RELEASE OF BIOLOGICALLY ACTIVE COMPOUNDS

[75] Inventors: Mircea A. Mateescu, Verdun; Vincent Lenaerts, Brossard; Yves Dumoulin, Boucherville, all of Canada

[73] Assignee: Labopharm, Inc., Quebec, Canada

[21] Appl. No.: 194,126

[22] Filed: Feb. 9, 1994

Related U.S. Application Data

[63] Continuation of Ser. No. 787,721, Oct. 31, 1991, abandoned, which is a continuation of Ser. No. 618,650, Nov. 27, 1990, abandoned.

[51] Int. Cl.⁶ .................................................. A61K 9/26
[52] U.S. Cl. .......................... 424/465; 424/484; 424/485; 424/486; 424/487
[58] Field of Search ................................ 424/465, 484, 424/485, 486, 487

[56] References Cited

U.S. PATENT DOCUMENTS

| | | | |
|---|---|---|---|
| 3,622,677 | 10/1971 | Short | 514/778 |
| 4,088,798 | 5/1978 | Michallis | 514/960 |
| 4,230,687 | 10/1980 | Sair et al. | 424/485 |
| 4,369,308 | 1/1983 | Trubiano | 514/960 |
| 4,451,452 | 5/1984 | Deibig et al. | 424/493 |
| 4,713,249 | 12/1987 | Schroder | 424/488 |
| 4,755,397 | 7/1988 | Eden et al. | 427/213.3 |
| 4,761,289 | 8/1988 | Shalati et al. | 424/468 |
| 4,812,445 | 3/1989 | Eden et al. | 514/60 |
| 4,814,182 | 3/1989 | Graham et al. | 424/484 |
| 4,933,185 | 6/1990 | Wheatley et al. | 424/461 |
| 4,952,402 | 8/1990 | Sparks et al. | 424/419 |
| 5,108,758 | 4/1992 | Allwood et al. | 424/468 |

*Primary Examiner*—John C. Bleutge
*Assistant Examiner*—Robert H. Harrison
*Attorney, Agent, or Firm*—Foley & Lardner

[57] ABSTRACT

The present invention is concerned with a solid slow release oral pharmaceutical dosage unit which comprises a solid dosage unit made up of an admixture of a therapeutic dosage of an orally effective pharmaceutical product and a cross-linked polymer of amylose with a cross-linking agent selected from 2,3 dibromopropanol and epichlorohydrin, wherein the cross-linking of the polymer has been carried out with from about 0.1 to about 10 g of cross-linking agent per 100 g of amylose.

29 Claims, No Drawings

USE OF CROSS-LINKED AMYLOSE AS A MATRIX FOR THE SLOW RELEASE OF BIOLOGICALLY ACTIVE COMPOUNDS

This application is a continuation of application Ser. No. 07/787,721, filed Oct. 31. 1991 abandoned, which is a continuation of Ser. No. 07/618,650, filed on Nov. 27, 1990, now abandoned.

FIELD OF THE INVENTION

The present invention relates to a slow release pharmaceutical tablet, and more particularly to a slow release pharmaceutical tablet incorporating a crosslinked polymer of amylose as the slow release matrix.

PRIOR ART

In the last two decades much interest has been paid to the development of monolithic devices for the controlled release of drugs by various routes of administration.

There are several types of polymers which have already been used as matrix for the release of drug. Thus, polymeric materials such as polyvinyl chloride, polyethylene polyamides, ethylcellulose, silicone, poly(hydroxyethyl methacrylate)PHEMA, other acrylic copolymers, polyvinylacetate-polyvinylchloride copolymers and other polymers were described as adequate matrix for tablet preparation (see for example U.S. Pat. No. 3,087,860; U.S. Pat. No. 2,987,445; and Pharm. Acta Helv., 1980, 55, 174–182, Salomon et al.

The controlled or slow release of some drugs is of a high importance for biopharmaceutical applications. There are various systems of slow release, mostly based on diffusion-controlled release or swelling control release mechanisms. Diffusion-controlled polymeric systems allow some prolongation of drug release but provide no real means of control since the release rate is not constant.

Recently, many efforts have been devoted to the development of systems able to release the drug at a constant rate, in other words, following zero-order kinetics, such as described in S.T.P. Pharma 1986, 2, 38–46 (Peppas et al.). The approach called 'swelling-controlled' systems consists in glassy polymers into which a water front penetrates at a constant rate. Behind this front, the polymer is in a rubbery state. Provided the drug diffusion coefficient in the rubbery polymer is much higher than in the glassy polymer, a zero order release can be achieved to a certain degree. However, the delivery rate is constant only for a limited fraction of the release, usually around 60% of the total amount of contained drug, and requires a low initial drug concentration.

Accordingly, it would be highly desirable to provide a slow release system following a zero-order kinetics, and allowing a controlled release of a drug at a constant rate until all the drug is released, whatever the concentration of the drug in the system is.

SUMMARY OF THE INVENTION

In accordance with the present invention there is now provided a solid slow release oral pharmaceutical dosage unit which comprises a solid dosage unit made up of an admixture of a therapeutic dosage of an orally effective pharmaceutical product and a cross-linked polymer of amylose with a cross-linking agent selected from 2,3-dibromopropanol and epichlorohydrin, wherein the crosslinking of the polymer has been carried out with from about 0.1 to about 10 g of cross-linking agent per 100 g of amylose.

In another aspect of the present invention, most of the particles of the cross-linked polymer of amylose with a cross-linking agent have a size that varies generally between about 25 and about 300 microns, but can be as high as 700 microns.

In a further aspect of the present invention, the pharmaceutical product is present in the tablet in an amount of from about 10 to 60% w/w.

DETAILED DESCRIPTION

Cross-linked amylose

The cross-linking of amylose is well known in the literature. For example, the desired cross-linking can be carried out in the manner described in BIOCHIMIE 1978, 60, 535–537 (Mateescu) by reacting amylose with epichlorohydrin in an alkaline medium. In the same manner, amylose can also be cross-linked with 2,3-dibromopropanol.

Essentially, the amylose is swollen in an alkaline medium such as sodium hydroxide and after homogenization, an appropriate amount of cross-linking agent is added. After complete homogenization, the reaction medium is transferred onto a water bath and heated for one hour at a temperature of from 40° to 45° C. and the temperature is then raised to from 60° to 75° C. for a further period of from 1 to 2 hours after which time the reaction is complete. The duration of heating can be varied as well as the amount of cross-linking agent used in the reaction.

The resulting cross-linked gel is then sieved in wet form and the granules ranging from about 25 to about 700 μm are collected for the preparation of the slow-release tablet of the present invention. The granules of 25 to about 300 μm representing at least 50% of the granules are selected for use in accordance with the present invention.

The preferred cross-linked polymers of amylose with epichlorohydrin (CLA) suitable for the purposes of the present invention are those where from about 0.1 to about 10 g of epichlorohydrin have been used to cross-linked 100 g of amylose. More preferred cross-linked polymers were obtained when from about 0.5 to 7.5 g of epichlorohydrin per 100 g of amylose were used.

In accordance with the present invention, it has been found that a polymer of amylose cross-linked with a cross-linking agent selected from 2,3-dibromopropanol and epichlorohydrin, wherein from about 0.1 to about 10 g of cross-linking agent have been used to cross-linked 100 g of amylose, are surprisingly and unexpectedly suitable for the slow-release of a large variety of drugs associated therewith. It has unexpectedly and surprisingly been found that the tablets prepared in accordance with the present invention are adapted to liberate the drug in a dose to linear release for a period of from 11 to 37 hours, or even more depending on the amount of epichlorohydrin used to cross-linked amylose.

Preparation of tablets

About 10 to 60% w/w of anhydrous theophylline was mixed with cross-linked amylose (CLA) in a shaking mixer for a few minutes. Tablets weighing about 500 mg each were obtained by compression in a hydraulic press at more than 0.15 T/cm$^2$. Tablets of 1.26 cm diameter and thickness of about 2.9 to about 4.5 mm can be obtained depending on the applied pressure, but various geometry can also be realized.

Hardness tests have also shown that it is not dependent on the crosslinking degree.

In order to illustrate the advantages of the present invention, the release of theophylline from CLA tablets was selected as a model for kinetic studies of the release. Obviously other drugs could be incorporated in the CLA tablets of the present invention and provide similar slow release characteristics, as long as there is no interactions between the drug and the CLA.

'In vitro' drug release from tablets

Tablets were placed individually in 1L distilled water at 37° C. in U.S.P. XX dissolution apparatus equipped with a rotating paddle (50 r.p.m.). Theophylline release was followed spectrophotometrically at 254 nm (Pharmacia single path monitor UV-1) and continuously recorded; a closed loop system and a peristaltic pump at a flow rate of 10.0 mL/min, were used.

CLA is an interesting polymer for the preparation of controlled release drug tablets. Advantages of this material include the easy manufacturing of tablets, the possibility of maintaining controlled release even at a high drug concentration in the tablet, and the relative independence of release kinetics from drug loading in certain limits. Furthermore, the CLA slow release matrix of the present invention has high biocompatability, and total 'in vivo' biodegradability. Also, tests have shown that the drug release kinetics are not influenced at pH values of from 1.5 to 11, which strongly suggest that the present release controlled system will be applicable in gastroenteric media.

The present invention will be more readily understood by referring to the following examples which are given to illustrate the invention rather than limit its scope.

EXAMPLE 1

Cross-linking of amylose with epichlorohydrin 10g of corn amylose are introduced, under agitation, in 35 mL 5N NaOH, at 0°–2° C. and homogenized at the same temperature, on an ice bath, for about 30 min. Then, 0.1 g of epichlorohydrin are slowly added, and the homogenization continued, for another 30 min on the ice bath. After complete homogenization, the recipient containing the reaction medium is transferred onto a water bath and heated for one hour at 40°–45° C., and then at 60°–75° C. for another 100 minutes, for completion of the reticulation reaction. During heating, 1–2 mL of water is added from time to time in order to avoid an advanced dehydration of the reaction medium. After the reticulation is accomplished, the cross-linked amylose gel is washed several times with distilled water for elimination of sodium hydroxide excess, until a pH value of 6 of the distilled water is reached. The CLA gel is sieved in wet form, retaining grains ranging between 25–75 μm, and then dried by treatment and subsequent decantation with increasing acetone concentration. The whole procedure is carried out over a period of several hours. The last step consists of washing the resulting solid with pure acetone, directly on a Büchner filter, followed by drying at air overnight.

The product prepared according to this Example will be referred to hereinafter as CLA-1.0.

A similar cross-linked polymer was obtained by substitution of 2,3-dibromopropanol for epichlorohydrin.

EXAMPLE 2

By proceeding in the same manner as in Example 1 and replacing the 0.1 g of epichlorohydrin by 0.4; 0.75; 1.2 and 2.0 g, there is obtained corresponding cross linked products hereinafter identified as CLA-4.0, CLA-7.5, CLA-12, and CLA-20.

EXAMPLE 3

Preparation of Tablets.

Anhydrous theophylline reagent grade (Baker) is mixed (10% w/w) with cross-linked amylose in Turbula shaking mixer for about 10 min. Tablets weighing about 500 mg each are obtained by compression in Carver hydraulic press at more than 2.4 T/cm$^2$, with a 1.26 cm diameter and thickness of 2.9 mm. The same procedure can be applied for different amounts of theophylline in the tablets. For example, tablets containing 10, 20, 30, 40, 50 and 60% w/w of theophylline were prepared.

EXAMPLE 4

'In vitro' drug release results. Equilibrium swelling

Equilibrium swelling of various types of CLA polymeric powder, CLA drug free tables and CLA containing 10% theophylline tablets are measured in water and various aqueous solvents at room temperature.

The tablets or the equivalent mass of 500 mg of CLA powder are placed in a 50 mL graduate cylinder to which 50 mL water or aqueous solvents are added. After 96 hours, the equilibrium swelling volume was read directly. The swelling is expressed as swollen volume per weight unit of initial dry material (mL/g). The swelling volume of the powders in water varied from 12 to 42 mL/g.

Analysis of theophylline release from CLA tablets

Theophylline release data are analyzed using the equation proposed by Peppas in Pharm. Acta Helv. 1985, 60, 110–111:

$$\frac{M_t}{M_\infty} = kt^n \text{ where}$$

$M_t$ - The amount released at $t$ $M_\infty$ - Total amount released $t$ - Time $k$ - Kinetic constant $n$ - Characterizes the release mechanism as summarized in table I

TABLE I

| Analysis of diffusional release mechanism | | |
|---|---|---|
| Diffusional release exponent (n) | Overall solute release mechanism | Time dependence of solute release rate (dMt/dt) |
| n = 0.5 | Fickian diffusion | $t^{-0.5}$ |
| 0.5 < n < 1.0 | Anomalous diffusion | $t^{n-1}$ |
| n = 1 | Case II transport | zero-order ($t^0$) |
| n > 1 | Super case II transport | $t^{n-1}$ |

In the above Table I, the Fickian diffusion is controlled by Fick's laws, and the release is in a hyperbolic function upon the time, and linear in function of $t^{1/2}$. In the anomalous diffusion, the release curve upon the time is somewhat between the hyperbolic and linear dependency. In Case II transport, the release curve is linear in function of the time, whereas Supercase II transport is for an exponential function of the release upon the time.

Table II shows examples of theophylline release from tablets initially containing 10 to 60% theophylline in CLA. Analysis of solute release data for CLA-1.0, CLA-4.0 and CLA-7.5 between $t_0$ ($t_0$=initial time) and t 90 (corresponding to 90% of total theophylline release) are also presented in Table II.

TABLE II

Kinetics parameters of 90% release of the initial theophylline amount

| Type of gel | Drug content % | Release time(hours) $M_t/M_\infty = 90\%$ | Kinetic parameter k* | Kinetic parameter n* |
|---|---|---|---|---|
| Amylose | 10 | 1.2 | 0.785 | 0.876 |
| CLA-1.0 | 10 | 37.0 | 0.129 | 0.537 |
| CLA-1.0 | 50 | 32.0 | 0.096 | 0.634 |
| CLA-1.0 | 60 | 24.0 | 0.013 | 0.551 |
| CLA-4.0 | 10 | 25.0 | 0.126 | 0.634 |
| CLA-4.0 | 40 | 24.0 | 0.162 | 0.531 |
| CLA-4.0 | 50 | 13.0 | 0.283 | 0.423 |
| CLA-7.5 | 10 | 11.5 | 0.182 | 0.662 |
| CLA-7.5 | 20 | 11.5 | 0.161 | 0.702 |
| CLA-7.5 | 30 | 7.0 | n.d. | n.d. |
| CLA-12.0 | 10 | 1.3 | 0.760 | 0.890 |
| CLA-20.0 | 10 | 0.7 | 1.330 | 1.210 |

*Kinetic parameters from Peppas equation
n.d. = No representative

These data are obtained when release of the theophylline occurs from all faces of the tablet. Most values of n are ranging between 0.5 and 1, which is indicative of an anomalous solute release mechanism, as illustrated in Table I. Indeed, the theophylline release from the CLA tablets of the present invention follow a generally close to linear dependency upon time, which is a characteristic of anomalous release type. Since there is no glassy/rubbery transition in the polymer used in accordance with the present invention, the deviation from a fickian behaviour cannot be explained by the 'swelling control' release mechanism as described in S.T.P. Pharma, (supra).

The theophylline powder is mixed with polymeric granules prior to compression. Thus the tablet consists in an agglomerate of polymeric granules surrounded by theophylline. This is completely different from the 'swelling control system' in which the drug is molecularly dispersed into a glassy polymer which turns into a rubbery one upon solvent penetration. When water penetrates into the tablet, the polymer hydrates and swells. CLA-1.0 has a low cross-linking degree and a small number of three-dimensional transversal glycerine bridges introduced by the crosslinking. As a consequence, it is assumed that an important number of hydrogen bounds can be created between neighbouring polymeric chains following the compression. The slow theophylline release from CLA-1.0 tablets could therefore be attributed to a slow water penetration due to the presence of numerous intragranular hydrogens bonds. At higher cross-linking ratios, the higher density of glyceric bridges of a total length of 8.64 Å (resulting from epichlorohydrin treatment) between adjacent amylose chains may prevent the network from coming near the distance necessary to form hydrogen bonds. Typically, this distance is about 5.6 Å.

On the other hand, following the introduction into water, the tablets made with CLA having a higher reticulation degree, e.g. CLA-12 and CLA-20, were totally disaggregated over a period of approximately 90 minutes. Consequently, theophylline release was faster and closer to linearity, with k=0.76 and n=0.890 for CLA-12 and with k=1.33 and n=1.21 for CLA-20 respectively (Table II).

It is interesting to note that small changes in the reticulation degree, for instance between CLA-7.5 and CLA-12, with swelling volumes of powders of 17.2 and 14.4 mL/g respectively, produce important differences in release kinetics, i.e. the release time decreased from 15 to 2 hrs. However, differences of the same order in the reticulation degree of CLA-12 and CLA-20, with swelling volumes of powders of 14.4 and 12.0 mL/g respectively, have no significant effect on the release kinetics, that is about 2 hours in both cases. These data confirm the importance of the hydrogen associations in the case of CLA-1.0, CLA-4.0 and CLA-7.5 tablets.

Accordingly, one can assume that at higher cross-linking degree of amylose, fewer hydrogen bonds are formed, thus not allowing good cohesion of the tablet. Upon swelling, individual polymeric granules separate and the drug is released too fast.

It is assumed that in the case of CLA-1.0, CLA-4.0 and CLA-7.5, hydrogen bonds are formed within polymeric granules as a result of the compression effort, ensuring good cohesion in the tablets, even under swollen state. This cohesion plays an important role in the control of the water penetration rate and in preventing the tablet from a rapid disintegration.

It is therefore assumed that the drug release is controlled partly by the water penetration forming new water-amylose hydrogen associations, which can even replace the amylose-amylose interchains hydrogen bonds. This behaviour plays a role in the deviation from the direct dependency of fickian diffusion mechanism. The presence of strong intragranular hydrogen bonds in the CLA-1.0, CLA-4.0 and CLA-7.5 tablets are confirmed by measuring equilibrium swelling of CLA in tablets and powder, using water and 8 M urea respectively, to demonstrate the formation of interchain hydrogen bonds. Table III illustrates the equilibrium swelling of various cross-linked amylose.

TABLE III

Equilibrum swelling of cross-linked amylose
(Swollen gel volume/initial dry polymer weight)

| Material | Equilibrum swelling in water (mL/g) | Equilibrum swelling (8M urea) mL/g | Ratio swelling (8M urea/water) |
|---|---|---|---|
| CLA-1.0 Powder | 42.0 | n.d. | n.d. |
| CLA-1.0 Tablet | 2.0 | n.d. | n.d. |
| Ratio* P/T | 21.0 | | |
| CLA-4.0 Powder | 22.0 | 34.0 | 1.5 |
| CLA-4.0 Tablet | 5.0 | 26.0 | 5.2 |
| Ratio* P/T | 4.4 | | |
| CLA-7.5 Powder | 17.2 | 23.0 | 1.3 |
| CLA-7.5 Tablet | 5.0 | 24.0 | 4.8 |
| Ratio* P/T | 3.4 | | |
| CLA-12 Powder | 14.4 | 24.0 | 1.6 |
| CLA-12 Tablet | 12.4 | 24.0 | 1.9 |
| Ratio* P/T | 1.16 | | |
| CLA-20 Powder | 12.0 | 24.0 | 2.0 |
| CLA-20 Tablet | 10.4 | 24.0 | 2.3 |
| Ratio* P/T | 1.15 | | | n.d. = No deposition of the gel

TABLE III-continued

Equilibrum swelling of cross-linked amylose
(Swollen gel volume/initial dry polymer weight)

| Material | Equilibrum swelling in water (mL/g) | Equilibrum swelling (8M urea) mL/g | Ratio swelling (8M urea/water) |
|---|---|---|---|

$$\text{Ratio* P/T} = \frac{\text{Swollen volume of CLA powder}}{\text{Swollen volume of CLA Tablet?}}$$

As shown in Table III, the swelling volumes of all CLA tablets and powder were higher in 8M urea than in water. For CLA-1.0 and CLA-4.0, the ratio P/T was higher than for all other CLA types, supporting the hypothesis of interchain hydrogen association following the compression. For each cross-linking degree, equilibrium swelling in water was more important for powders than for tablets, probably because of the new intragranular hydrogen bonds created by compression. Thus, the ratio of swelling in 8M urea/water was significantly more pronounced in the case of lower reticulated CLA tablets which develops more intragranular hydrogen bonds than amylose having a higher reticulation degree. For instance, the values of the ratio swelling were 5.2 for CLA-4.0 tablets, and then decreasing to 1.9 for CLA-12 and to 2.3 for CLA-20 tablets. Therefore, these results are consistent with the hypothesis that tablets of lower cross-linking of amylose show good cohesion because of strong intragranular hydrogen bonds.

Since granullometrics and compression forces were also similar, tablets should present no significant difference in consistence. It is therefore unlikely that the observed difference in theophylline release kinetics could result from the effect of porosity on water penetration kinetics. Furthermore, the specific volume (42 mL/g) of dried CLA-1.0 powder was the highest, while the swelling of CLA-1.0 tablets was the lowest, and the theophylline release from this type of product was the slowest. Therefore, these results confirm that hydrogen associations are implied in the release control, rather than the porosity of CLA.

The influence of theophylline content in tablets on the drug release kinetics was also studied. In all cases, the yield of release was more than 95% in various kinetic conditions, between $t_0$ and $t_{90}$ of total theophylline release, depending on the reticulation degree and the drug content of the tablet. The release kinetics were partially similar at about 10–20% of theophylline for CLA-7.5; 10 to 40% of theophylline for CLA-4.0 and 10–50% of theophylline for CLA-1.0. This observation is consistent with the fact that these tablets are neither behaving like conventional hydrophillic matrix nor like 'swelling-controlled' systems. Indeed, in this last case, doubling the drug concentration would have modified the release kinetics more extensively. At the maximum capacities of drug content in the tablets, the release was much faster and showed irregular kinetics (Table II). Tablets of CLA-1.0, CLA-4.0 and CLA-7.5 containing a drug concentration higher than the maximum capacity were also partially disaggregated. The high amount of drug between polymeric granules probably caused insufficient cohesion, therefore leading to partial desaggregation.

Finally, the release of theophylline from pure amylose tablets was studied. The release is fast (1–2 hours when k=0.785, n=0.876), accompanied by erosion of the tablet. Furthermore, the release of theophylline from non crosslinked amylose tablets is quite similar to the release from CLA-12 and CLA-20 tablets. This fast release in the case of non cross-linked amylose demonstrates the importance of the particular three-dimensional structure, in which the interchain hydrogen bonds play a major role in the drug release rate.

From this dependence between the release time and the reticulation degree, evidence is given that for the low reticulation degrees, between 0 and 10%, the interchain hydrogen bonding is maximal, and seems to participate in the control of the theophylline release.

What is claimed is:

1. A solid controlled release oral pharmaceutical dosage unit in the form of a tablet consisting essentially of a compressed blend of 10 to 60% by weight of the tablet of a dry powder of a pharmaceutical product, and a corresponding amount of 40 to 90% by weight of the tablet of a dry powder consisting essentially of amylose cross-linked with a cross-linking agent selected from the group consisting of 2,3-dibromopropanol and epichlorhydrin, wherein the cross-linking has been carried out with from about 0.1 to about 2.5 grams of crosslinking agent per 100 grams of amylose, wherein at least 50% of said cross-linked amylose has a particle size of from about 25 to about 200 microns.

2. A solid controlled release pharmaceutical dosage unit in the form of a tablet consisting essentially of a compressed blend of 10 to 50% by weight of the tablet of a dry powder of a pharmaceutical product, and a corresponding amount of 50 to 90% by weight of the tablet of a dry powder consisting essentially of amylose cross-linked with epichlorhydrin, wherein the crosslinking has been carried out with from about 0.5 to about 2.5 grams of epichlorhydrin per 100 grams of amylose, wherein at least 50% of said cross-linked amylose has a particle size of from about 25 to about 700 microns.

3. A solid controlled release pharmaceutical dosage unit according to claim 1, wherein the unit has been formed by compression of said powders under compression of at least 0.15 T/cm$^2$.

4. A solid controlled release pharmaceutical dosage unit according to claim 1, wherein the cross-linking has been carried out with from 1.0 to 4.0 grams of cross-linking agent per 100 grams of amylose.

5. A solid controlled release pharmaceutical dosage unit according to claim 1, wherein the cross-linking has been carried out with from 4.0 to 7.5 grams of cross-linking agent per 100 grams of amylose.

6. A solid controlled release pharmaceutical dosage unit according to claim 1, wherein the cross-linking has been carried out with less than 1.0 grams of cross-linking agent per 100 grams of amylose.

7. A solid controlled release pharmaceutical dosage unit according to claim 1 which, when placed in one liter of 37° C. water per 500 mg of dosage unit weight, releases 90% of the pharmaceutical product into the water in not less than about 7.0 hours.

8. A solid controlled release pharmaceutical dosage unit according to claim 1 which, when placed in one liter of 37° C. water per 500 mg of dosage unit weight, releases 90% of the pharmaceutical product into the water in not less than about 11.5 hours.

9. A solid controlled release pharmaceutical dosage unit according to claim 7, wherein the rate of release is substantially independent of the amount of said pharmaceutical product in said dosage unit and said release is close to linear over time.

10. A solid controlled release pharmaceutical dosage unit according to claim 2, wherein the unit has been formed by compression of said powders under compression of at least 0.15 T/cm$^2$.

11. A solid controlled release pharmaceutical dosage unit according to claim 2, wherein the cross-linking has been carried out with from 1.0 to 4.0 grams of cross-linking agent per 100 grams of amylose.

12. A solid controlled release pharmaceutical dosage unit according to claim 2, wherein the cross-linking has been carried out with from 4.0 to 7.5 grams of cross-linking agent per 100 grams of amylose.

13. A solid controlled release pharmaceutical dosage unit according to claim 2, wherein the cross-linking has been carried out with less than 1.0 grams of cross-linking agent per 100 grams of amylose.

14. A solid controlled release pharmaceutical dosage unit according to claim 2 which, when placed in one liter of 37° C. water per 500 mg of dosage unit weight, releases 90% of the pharmaceutical product into the water in not less than about 2.0 hours.

15. A solid controlled release pharmaceutical dosage unit according to claim 2 which, when placed in one liter of 37° C. water per 500 mg of dosage unit weight, releases 90% of the pharmaceutical product into the water in not less than about 11.5 hours.

16. A solid controlled release pharmaceutical dosage unit according to claim 14, wherein the rate of release is substantially independent of the amount of said pharmaceutical product in said dosage unit and said release is close to linear over time.

17. A solid controlled release pharmaceutical dosage unit according to claim 10 which, when placed in one liter of 37° C. water per 500 mg of dosage unit weight, releases 90% of the pharmaceutical product into the water in not less than about 2.0 hours.

18. A solid controlled release pharmaceutical dosage unit according to claim 17, which when placed in one liter of 37° C. water per 500 mg of dosage unit weight, releases of the pharmaceutical product into the water in not less than about 11.5 hours.

19. A solid controlled release pharmaceutical dosage unit according to claim 18, wherein the rate of release is close to linear over time.

20. A solid controlled release pharmaceutical dosage unit according to claim 17, wherein the rate of release is substantially independent of the amount of said pharmaceutical product in said dosage unit.

21. A method for imparting sustained release to a pharmaceutical product, comprising the steps of:

(a) providing the pharmaceutical product in a dry powder form;

(b) blending the pharmaceutical product powder with a powder consisting essentially of amylose crosslinked with a cross-linking agent selected from the group consisting of 2,3-dibromopropanol and epichlorhydrin, wherein the cross-linking has been carried out with from about 0.1 to about 7.5 grams of cross-linking agent per 100 grams of amylose and wherein at least 50% of said crosslinked amylose has a particle size of from about 25 to about 700 microns, and (c) compressing the blend to form a tablet.

22. A method according to claim 21, wherein, step (b) comprises mixing the pharmaceutical product in an amount of from 10 to 60% by weight of the tablet with the cross-linked amylose in an amount of from 40 to 90% by weight of the tablet.

23. A method according to claim 21, wherein, step (b) comprises mixing the pharmaceutical product in an amount of from 10 to 50% by weight of the tablet with the cross-linked amylose in an amount of from 50 to 90% by weight of the tablet.

24. A method according to claim 21, wherein the cross-linking agent is epichlorhydrin.

25. A method according to claim 21, wherein the compression of step (c) is at least 0.15 T/cm$^2$.

26. A method according to claim 21, wherein step (b) is carried out with from about 0.5 to about 2.5 g of epichlorhydrin per 100 g of amylose.

27. A method according to claim 21, wherein step (b) has been carried out with from 1.0 to 4.0 grams of crosslinking agent per 100 grams of amylose.

28. A method according to claim 21, wherein step (b) is carried out with from 4.0 to 2.5 grams of cross-linking agent per 100 grams of amylose.

29. A method according to claim 21, wherein step (b) is carried out with less than 1.0 grams of cross-linking agent per 100 grams of amylose.

* * * * *

UNITED STATES PATENT AND TRADEMARK OFFICE
CERTIFICATE OF CORRECTION

PATENT NO. : 5,456,921
DATED : October 10, 1995
INVENTOR(S) : MATEESCU et al.

It is certified that error appears in the above-indentified patent and that said Letters Patent is hereby corrected as shown below:

```
Column 8, Claim 1, line 18, change "2.5" to read --7.5--;
                  line 21, change "200" to read --700--.

Column 8, Claim 2, line 29, change "2.5" to read --7.5--.
```

Signed and Sealed this

Thirtieth Day of July, 1996

Attest:

BRUCE LEHMAN

*Attesting Officer*   *Commissioner of Patents and Trademarks*